though not necessary to the invention.

United States Patent [19]
Adair

[11] Patent Number: 5,732,712
[45] Date of Patent: Mar. 31, 1998

[54] STERILE ENCAPSULATED OPERATING ROOM VIDEO MONITOR AND VIDEO MONITOR SUPPORT DEVICE

[76] Inventor: Edwin L. Adair, 317 Paragon Way, Castle Pines Village, Colo. 80104

[21] Appl. No.: 819,574

[22] Filed: Mar. 14, 1997

Related U.S. Application Data

[63] Continuation-in-part of Ser. No. 678,810, Jul. 12, 1996.

[51] Int. Cl.$^6$ .................................................. A61G 15/00
[52] U.S. Cl. .......................... 128/845; 128/849; 128/853
[58] Field of Search ................................. 128/849–856; 600/121, 122; 355/230, 231

[56] References Cited

U.S. PATENT DOCUMENTS

| | | | |
|---|---|---|---|
| 4,341,222 | 7/1982 | Gardineer | 128/915 |
| 5,129,397 | 7/1992 | Jingu et al. | 128/660.01 |
| 5,170,790 | 12/1992 | LaCoste et al. | 128/660.01 |
| 5,429,142 | 7/1995 | Szubo | 128/849 |
| 5,433,221 | 7/1995 | Adair | 128/849 |
| 5,490,524 | 2/1996 | Williams | 128/849 |
| 5,543,832 | 8/1996 | Oravecz et al. | 348/65 |

OTHER PUBLICATIONS

Sharp Corporation, *Color Display Modules*, Jan., 1995, pp. 1–13.
Sony Corporation, 8.6" *LCD Monitor Module*, SEU–2092, pp. 1–2.
Sony Corporation, 10.4" *LCD Monitor Module*, LMD–1040XC, pp. 1–2.

*Primary Examiner*—Michael A. Brown
*Attorney, Agent, or Firm*—Fields and Johnson, P.C.

[57] ABSTRACT

A sterile operating room video monitor and video monitor support device are provided to enable a surgeon to more easily conduct endoscopic procedures. A lightweight self-contained monitor module is provided to enable the surgeon to easily manipulate the image on the video monitor of a surgical area. A video support stand which secures the video monitor in the sterile operating field allows a surgeon to precisely place the video monitor at a desired position. The video support stand includes a monitor mount which may have a plurality of apertures communicating with a source of vacuum to hold a sterile drape tightly over the monitor module screen. Alternatively, the drape may be eliminated, and a close tolerance fit is made between the monitor mount and video monitor securing it in the sterile field. This invention allows positioning of the video monitor in the natural line of sight of the surgeon as he or she performs an endoscopic procedure.

7 Claims, 6 Drawing Sheets

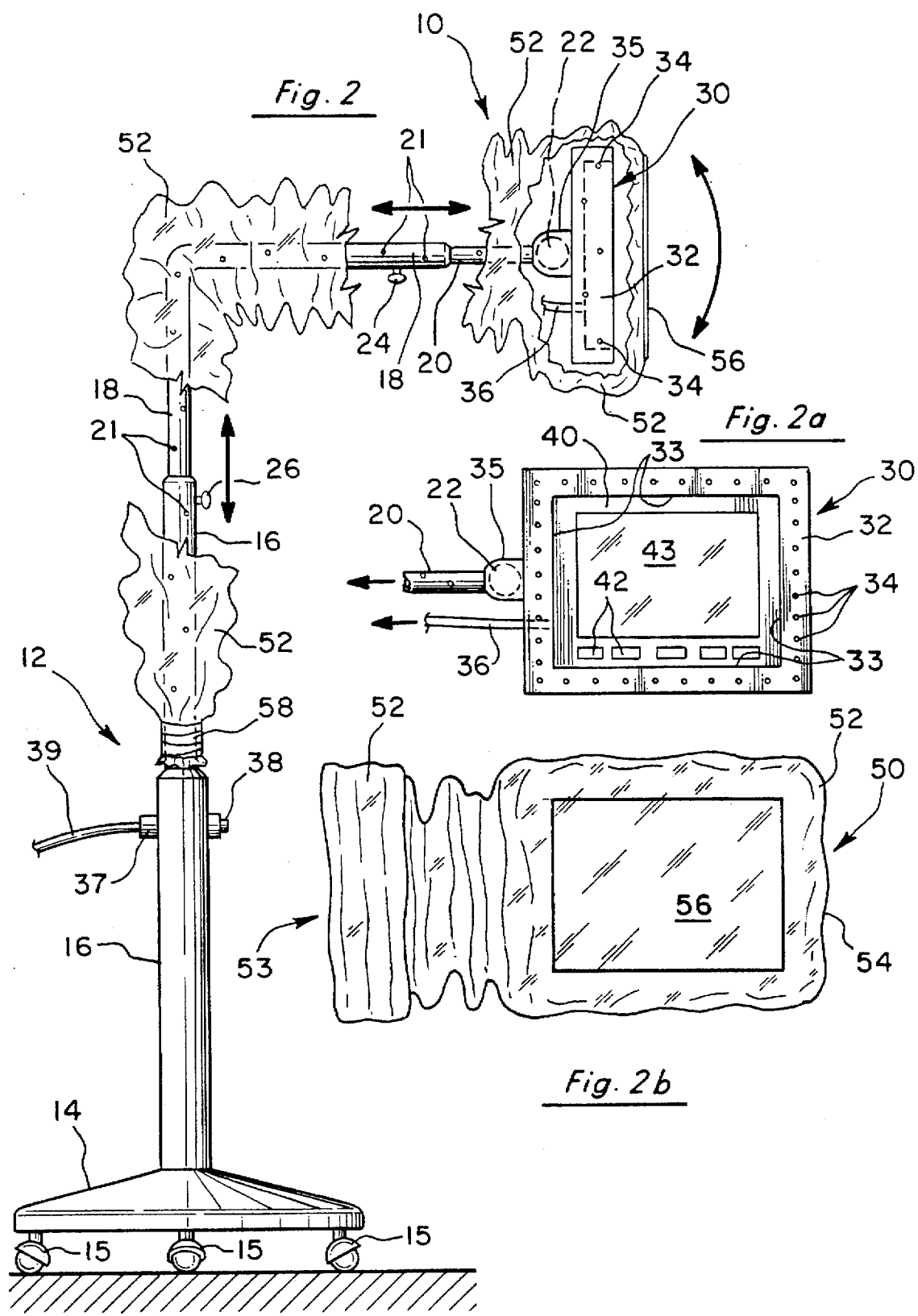

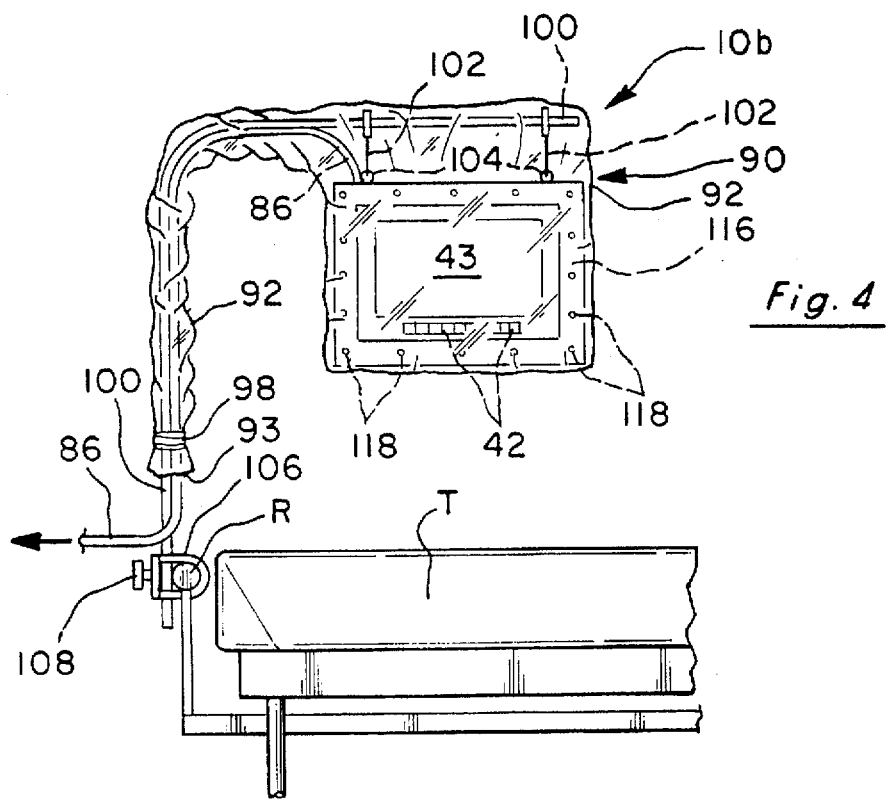
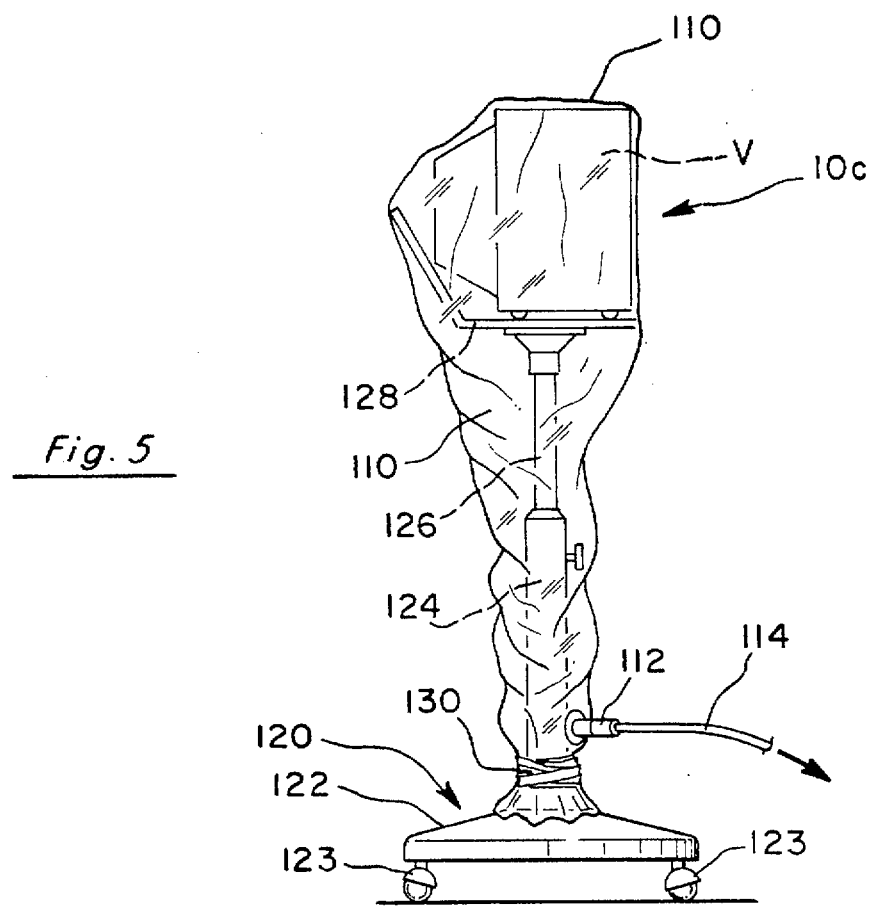

STERILE ENCAPSULATED OPERATING ROOM VIDEO MONITOR AND VIDEO MONITOR SUPPORT DEVICE

TECHNICAL FIELD

This invention is a continuation-in-part application of U.S. Ser. No. 08/678,810, filed Jul. 12, 1996 and entitled "Sterile Encapsulated Operating Room Video Monitor and Video Monitor Support Device."

This invention relates to an apparatus which provides a visual display of a surgical site, and more particularly, to a sterile encapsulated operating room flat panel video monitor and flat panel video monitor support used in conjunction with an endoscopic camera and instrument to provide an image of a surgical area.

BACKGROUND ART

Endoscopic procedures have become the standard in modern medicine for conducting surgical procedures which are minimally invasive. Prior to the development of endoscopic procedures, surgery required direct visual access to the surgical area which oftentimes resulted in extreme trauma to the patient due to large incisions and the like. With the development of endoscopic instruments which include video cameras that can transmit an image of the surgical site to a video display, surgical procedures can be conducted in a less invasive manner. Although endoscopic procedures represent a great leap forward in terms of minimizing patient trauma, endoscopic procedures using video displays have also resulted in new problems.

One prerequisite for successful endoscopic procedures is that the surgeon must be skilled with the use of the endoscope so that the endoscope itself does not cause unintentional damage to the patient's tissues. In most endoscopic procedures conducted today, the surgeon may view a standard television (TV) monitor or video screen which displays an image of the surgical site as photographed by a video camera positioned within or adjacent the endoscopic instrument. One problem created by the use of endoscopes with integral video cameras is that the surgeon must be able to precisely manipulate the endoscope within the patient's body while looking away from the patient and toward the remote TV monitor. Since the standard TV monitor must be placed at a location substantially remote from the patient's body, surgeons have had to develop particular dexterity and skill in ensuring that the endoscope does not unintentionally damage body tissues during the surgical procedure.

Another problem associated with endoscopic procedures utilizing TV monitors or video screens is that the surgeon is dependent upon another person to control the exact type of image displayed on the TV monitor. More particularly, the surgeon may be able to adjust the focus of the image by a dial located upon the endoscope; however, neither the endoscope nor the camera attached to the endoscope have controls to vary the brightness, contrast or magnification of the image. Accordingly, the surgeon must direct operating room personnel to adjust the visual display as desired.

Another problem associated with the advent of endoscopic procedures utilizing video equipment is that since additional equipment is brought into the operating room, there is a concern for preventing contamination by the equipment of the sterile field of the operating room. Electronic equipment including TV monitors tend to naturally induce or create an electric charge causing dust which contains microbes to collect on this equipment wherein such microbes can then be transmitted to the sterile operating field of the operating room or surgical area. It has been found that a surgeon placing his hand near a TV monitor displaying an image of the surgical area can attract undesirable microbes via the differential in electrostatic charge between the surgeon's hand and the TV or monitor screen.

Additionally, standard TV monitors and their associated controls are typically large and heavy and difficult to manipulate within the operating room. Accordingly, this equipment cannot be placed directly adjacent to the patient to enhance the surgeon's ability to manipulate the endoscopic instrument in a visually aligned position with respect to the surgical area.

Each of the above-identified disadvantages of current endoscopic procedures utilizing standard video equipment is overcome by the invention claimed herein.

DISCLOSURE OF THE INVENTION

According to the present invention, a sterile encapsulated operating room flat panel video monitor and flat panel video monitor support device are provided. The use of the operating flat panel video monitor and corresponding monitor support device is particularly suited for surgical procedures such as laparoscopy, thoracoscopy, interventional radiology procedures, interventional cardiology procedures, interventional neurological procedures, endoscopic plastic surgery, flexible gastrointestinal endoscopic procedures, endoscopic dental surgery, and endoscopic endourology procedures, to name just a few. In the first two embodiments of the invention, a video support stand is provided for mounting a monitor mount thereto. Received within the monitor mount is a monitor module or flat panel video screen which shows images of a surgical site via images photographed by a video camera in communication with an endoscopic instrument. A sterile drape is positioned over the monitor mount securing the monitor module, and the drape extends over a desired length of the video support stand and trailing cables of the endoscopic instrument. Thus, the monitor module may be placed in the sterile field of the operating room enabling the surgeon to align the monitor module with respect to the specific surgical site. Adjustments are provided on the video support stand and on the monitor mount to enable the monitor module to be positioned at a precise location with respect to the surgical area. In one preferred embodiment, the monitor module takes the form of a very thin and lightweight video monitor. A plurality of apertures may be formed on the surface of the monitor mount which communicate with a source of vacuum in order that a vacuum can be drawn on the interior open space covered by the drape so that the drape is drawn tightly against the monitor module screen. A tight fitting drape over the video support stand and monitor mount reduces the possibility that the sterile drape will be ripped or torn during use, and any distortion of the visual image displayed on the monitor module will be minimized since the drape will be held tightly against the monitor module screen.

In another embodiment, the sterile operating room flat panel video monitor and flat panel video monitor support device can be directly mounted to the side rail of the operating room table enabling the support device to be placed in any number of differing positions adjacent or upon the patient. In this embodiment, a support arm of the device attaches to the side rail by means of a clamp or bracket and the monitor mount is suspended over the operating room table at a desired location with respect to the patient. As with the previous embodiments, a sterile drape is placed over the monitor mount containing the monitor module and extends over the support arm. A vacuum line extending adjacent the support arm communicates with apertures formed in the monitor mount so that the sterile drape may be snugly secured against the screen of the monitor module. Alternatively, a standard surgical drape can be used to cover the support arm and a separate drape can be used to cover the monitor mount and monitor module which are then mountable to the draped support arm.

In yet another embodiment, a support assembly is provided which includes a support platform for securing a standard TV monitor or laptop computer. A large drape is placed over the TV monitor/laptop computer and extends over a desired length of the support assembly. A vacuum port is formed on the sterile drape for attachment to an external vacuum line.

Additional advantages of this invention will become apparent from the description which follows, taken in conjunction with the accompanying drawings.

BRIEF DESCRIPTION OF THE DRAWINGS

FIG. 2 is a side elevation view of a first embodiment of the sterile encapsulated operating room flat panel video monitor and flat panel video monitor support device of this invention;

FIG. 2a is an enlarged front elevation view of a video monitor module mounted to the video monitor support according to the first embodiment;

FIG. 2b is a front elevation view of a sterile drape which covers the video monitor support of the invention;

FIG. 4 is a front elevation view of a third embodiment of the encapsulated device of this invention; and FIG. 5 is a side elevation view of a fourth embodiment of the encapsulated device of this invention.

BEST MODE FOR CARRYING OUT THE INVENTION

Figure 1:
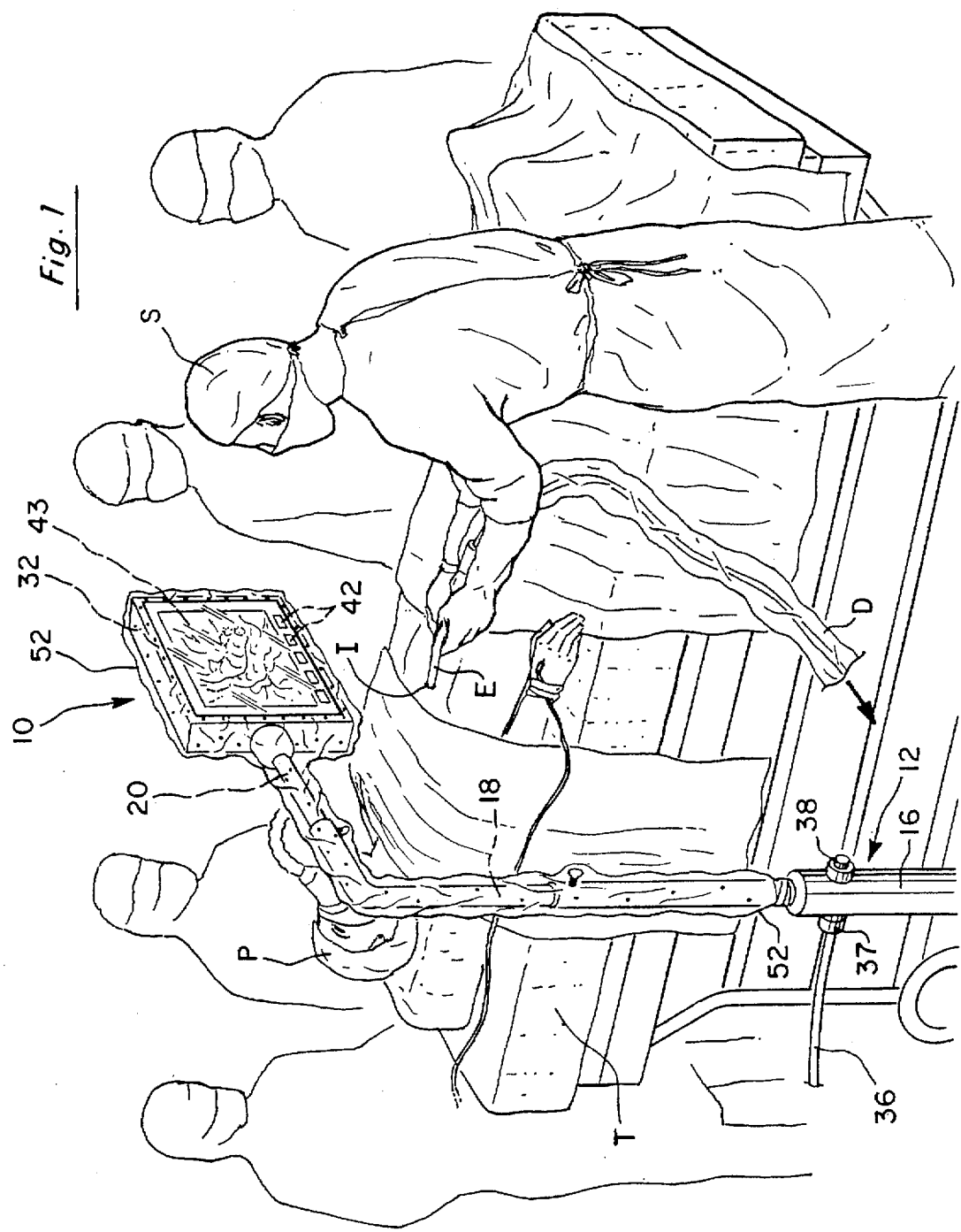
FIG. 1 is a perspective view of a sterile encapsulated operating room flat panel video monitor and flat panel video monitor support device while being used in a surgical procedure.

According to a first embodiment as shown in FIGS. 1 and 2, the sterile encapsulated operating room flat panel video monitor and flat panel video monitor support device 10 includes a video support stand 12 for securing a video monitor module or video monitor 40 thereto. The video support stand 12 includes a base 14 which connects to a vertical support 16. At the free upper end of vertical support 16 is attached an angular support arm 18 which has a vertical section received in vertical support 16 and a horizontal section. As shown in FIGS. 1 and 2, vertical support 16 may comprise a larger lower section and a smaller upper section. Alternatively, vertical support 16 may be made of a single member of sufficient size to adequately support arm 18 and monitor module 40. As shown, support arm 18 may be vertically adjusted by use of vertical support adjustment 26 which may be in the form of a wing nut or the like. The horizontal free end of support arm 18 may include a telescopic portion 20 which enables the support arm to be adjusted in a horizontal direction. Arm adjustment 24 is provided to adjust the length of telescopic portion 20 which protrudes from the horizontal free end of support arm 18. A plurality of casters 15 or other wheeled mechanisms attach to the base 14 in order that the video support stand 12 may be conveniently moved from one location to another. A support arm ball 22 is attached to the free end of the telescopic portion 20 and serves as a point of universal rotation for the monitor module 40, as explained below.

As seen in FIGS. 2 and 2a, monitor mount 30 attaches to ball 22 of the telescopic portion 20 by means of socket 35. Ball 22 and socket 35 serve as a ball and socket joint which enables the monitor mount 30 to be rotated in an infinite number of positions about ball 22.

As shown in FIG. 2a, the support arm ball 22 and socket 35 may be located to the side of the monitor mount 30 or, as shown in FIG. 2, the ball 22 and socket 35 may be placed on the back side of monitor mount 30.

Monitor mount 30 includes a monitor mounting frame 32 which is configured to receive the appropriate monitor module 40. As shown in FIGS. 2 and 2a, the monitor mounting frame 32 may receive a monitor module such as those manufactured by Sony, known as "LCD Monitor Modules," which have particularly thin bodies and are lightweight. For example, Model No. SEU-2092, manufactured by Sony, is a chassis-type LCD monitor module having a 58 mm depth and weighing less than 2,000

As shown in FIG. 2a, monitor mount 30 may be of a box-like configuration for receiving the monitor module 40 through a front opening sized to receive the monitor module. In use, a sterile drape 50 is placed over the monitor mount 30 securing the monitor module 40 and over a desired length of angular support arm 18 and vertical support 16. Sterile drape 50 is constructed of a substantially transparent, liquid and gas impermeable material such as polyurethane or the like. Sterile drape 50 comprises a flexible body 52, a closed distal end 54 which lies adjacent to the monitor module 40, and an open proximal end 53 which may be sealed against the support stand 12 by means of tape or adhesive 58.

The drape 50 may be constructed of a single type of material or, alternately, the drape may include a screen or monitor portion 56 which is made of a material which is highly transparent and is particularly useful in acting as a window through which to view the monitor module screen 43. This screen or monitor portion may be rigid or semi-rigid and sized to fit over screen 43. Acrylic or Lexan are examples of suitable materials for making the monitor portion 56. Such a screen portion 56 may additionally be coated with an anti-fogging or anti-glare agent to ensure that the monitor module screen 43 remains easily viewed under different conditions within the operating room.

A plurality of apertures 34 may be formed in monitor mounting frame 32. Each of the apertures communicate with vacuum line 36 via internal passages (not shown) formed in the mounting frame 32. For purposes of illustration, vacuum line 36 is shown as being positioned exteriorly of telescopic portion 20; however, vacuum line 36 may be placed inside telescopic portion 20 and be routed through support arm 18 and vertical support arm 16. The free end of internal vacuum line 36 may then be connected to vacuum fitting 37. An external vacuum line 39 may be connected to the opposite side of vacuum fitting 37, the external vacuum line communicating with a source of vacuum (not shown) such as a standard operating room vacuum pump or to a wall suction unit communicating with a Hospital Central Vacuum system. Alternatively, a vacuum pump may be incorporated within the structure of the video support stand 12 instead of using an external vacuum source. For example, the vacuum pump could be mounted on base 14 or be secured within vertical support 16.

The purpose of apertures 34 is to enable a vacuum to be drawn on 10 the interior open space defined by the interior surface of the sterile drape so that the sterile drape 50 may be tightly held against the screen 43 of the monitor module 40. This tight fit ensures that there is no visual distortion of the image shown on the screen 43 of the monitor module 40. Furthermore, the tight fit of the sterile drape 50 around the monitor mount 30 and monitor module 40 reduces the possibility that the sterile drape 50 will be inadvertently torn by contact during surgery. By reducing the possibility of tearing the drape, the sterility of the operating room field is better preserved.

It may also be desirable to provide a plurality of apertures 21 along the length of the vertical support 16, angular support arm 18 and/or the telescopic portion 20. These additional apertures can assist in ensuring that a uniform vacuum is experienced throughout the interior open space within the sterile drape 50. Apertures 21 may also communicate with internal vacuum line 36. Alternatively, vacuum line 36 may be eliminated and apertures 21 and 34 may simply communicate with vacuum fitting 37 through the hollow interior of video support stand 12. Conveniently, a vacuum switch 38 is provided on the vertical support 16 and is electrically connected to the vacuum pump in a conventional fashion, enabling operating room personnel to control the vacuum drawn on the sterile drape 50. In lieu of the use of a vacuum to secure the drape 50 against the monitor mount 30, the screen or monitor portion 56 may be rigid and sized to fit for engagement with the exposed interior edges defining the front opening thereof. Such an engagement may be of a friction-type fitting or snap configuration so that the screen portion 56 enables the monitor module screen 43 to be viewable under different conditions within the operating room. Accordingly, the remaining portion of the drape 50 may simply be extended over the remaining portion of monitor mount 30 and secured thereto by an appropriate tape or adhesive. Positively engaging the screen portion 56 with mounting frame 32 of the monitor mount ensures the viewability of the module 43 yet eliminates the need to draw a vacuum on the drape 50.

Figure 2C:
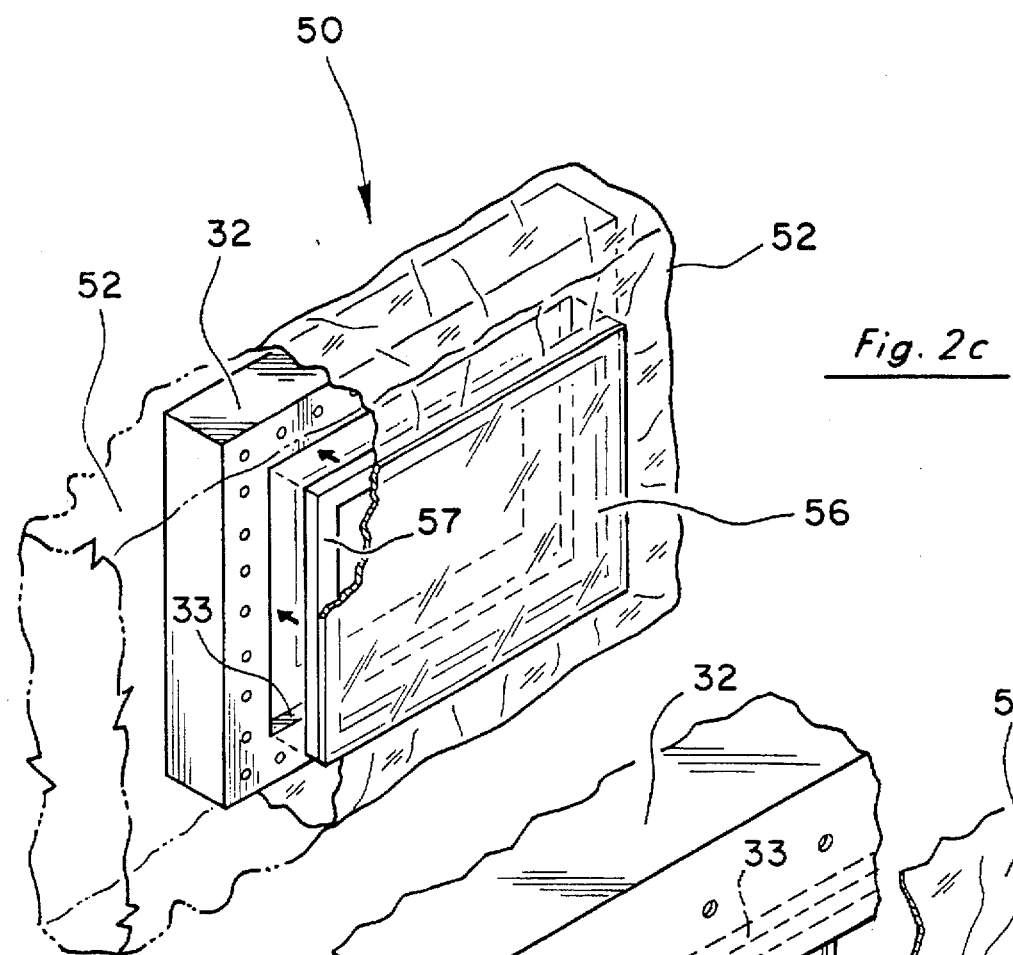
FIG. 2c is a fragmentary perspective view of a modified sterile drape which may cover the video monitor support of this invention.
Figure 2D:
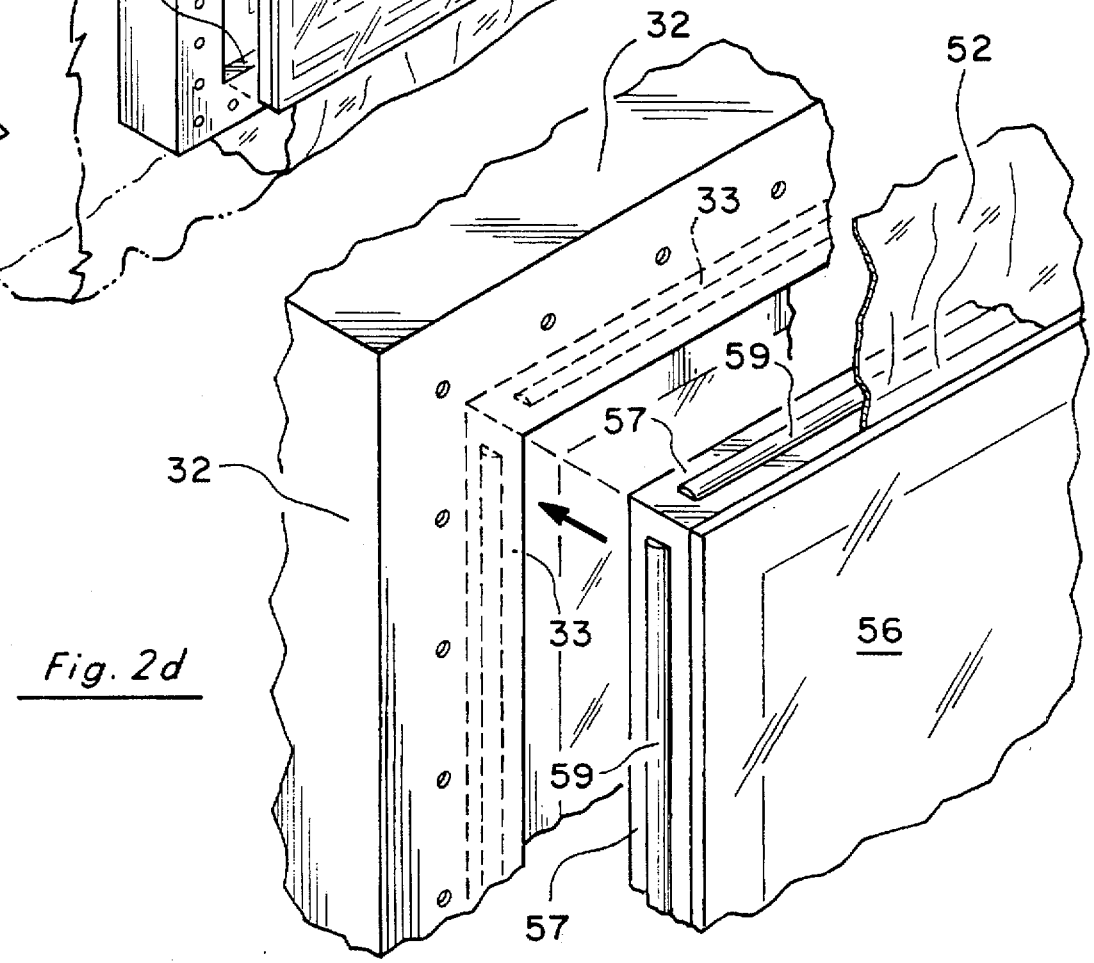
FIG. 2d is a fragmentary perspective view of another modified sterile drape which may cover the video monitor support of this invention.

In yet another preferred embodiment of the drape 50, the screen portion 56 may include a plurality of magnets (not shown) which hold the screen portion 56 firmly against the mounting frame 32. The frame 32 may be made of a ferrous material. Those skilled in the art can envision other methods by which a rigid or semi-rigid screen portion 56 may be secured over the module screen 43 without requiring a source of vacuum to be pulled on the drape 50. For example, as illustrated in FIGS. 2c and 2d, the screen or monitor portion 56 may include a thickened outer edge 57 which engages the interior exposed edges 33 of the monitor mounting frame 32. More specifically, when the screen or monitor portion is made of a substantially rigid material, the outer edge 57 of the monitor portion 56 may be sized to provide a close tolerant fit within exterior exposed edges 33 so as to securely fasten the monitor portion 56 over the monitor module screen 43. As further illustrated in FIG. 2d, the thickened outer edge 57 may include a ridge, tab, or generally raised portion 59 which further ensures that the monitor portion 56 is securely engaged with the exposed edges 33 of the mounting frame 32. The structure 59 may be so configured to enable a "snap fit" with the exposed edges 33. Additionally, the interior exposed edges 33 of the mounting frame 32 may include a recess or groove (not shown) for receiving the structure 59 formed on outer edges 57.

Monitor module 40 may include a plurality of membrane switches 42 which are located adjacent to the monitor module screen 43. The membrane switches may be wired to control desired video functions such as contrast, magnification and brightness, or to control other functions such as the printing of an image viewed on the monitor screen via a communicating printer, or to manipulate the sequence of images displayed by "freezing" images or arranging images in a desired sequential manner. Accordingly, the surgeon may directly control the type of image being viewed without having to instruct other operating room personnel as to the type of desired image to be viewed. Furthermore, since the monitor module 40 is isolated from the sterile operating field via the drape 50, the surgeon may freely manipulate the image by switches 42 without concern for loss of sterility. In lieu of membrane switches 42, the monitor module 40 may incorporate touch screen functioning wherein the surgeon or operating room personnel touch the monitor module screen 43 based upon the particular setup of the touch screen function(s).

Monitor modules manufactured by Sony and other manufacturers, such as Texas Instruments, Xerox, Sharp and Polaris, are self-contained units in that the monitor modules require, at most, a single communication cable which communicates with a video camera. Some manufacturers make monitor modules which require no communication cables and communicate with a video camera system by means of infrared, radio, or other electromagnetic signaling. Thus, it shall be understood that the monitor modules of the invention do not necessarily require any communication cables in order to produce an image of the surgical site.

Figure 3:
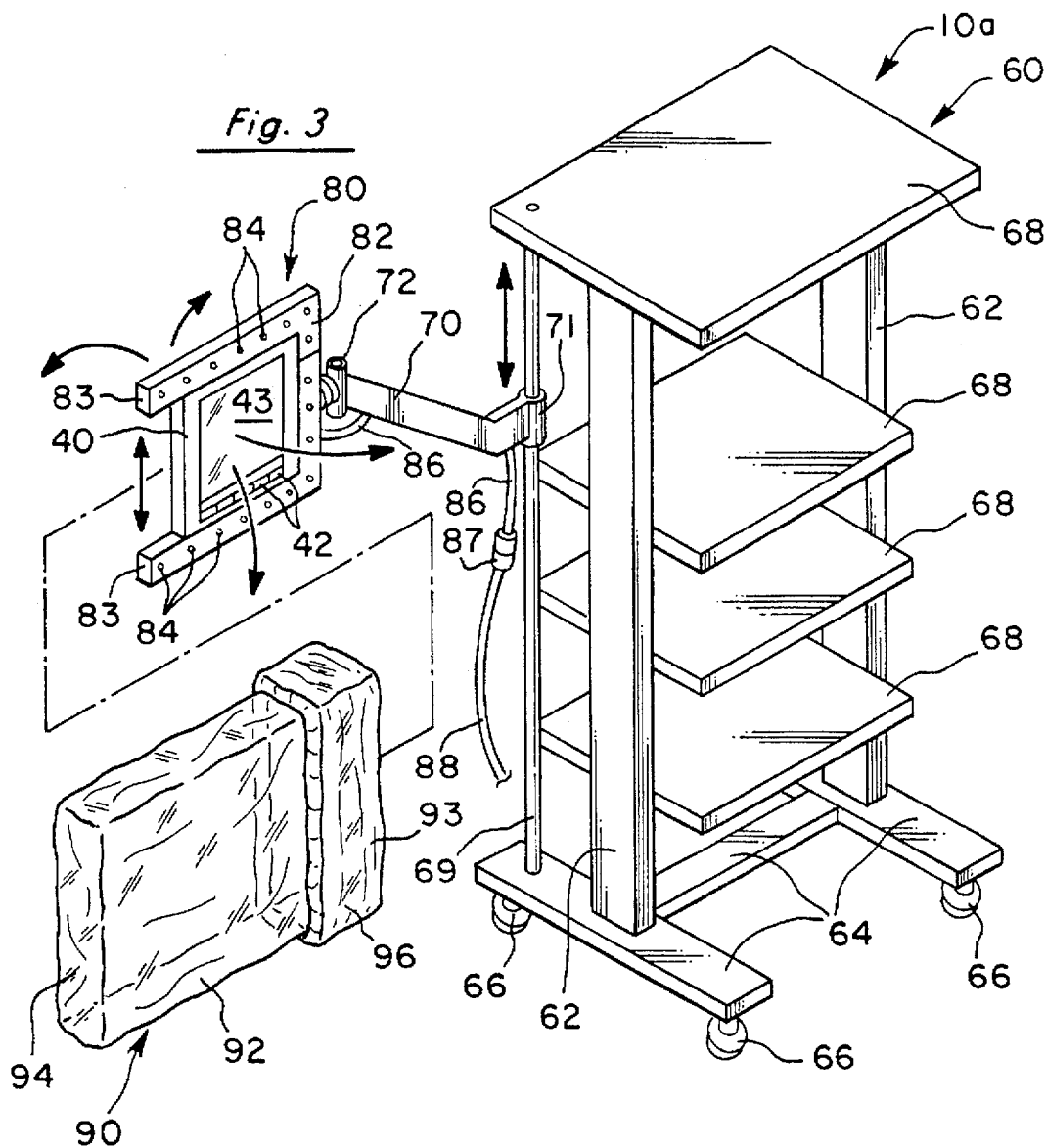
FIG. 3 is a perspective view of a second embodiment of the sterile encapsulated operating room flat panel video monitor and flat panel video monitor support device of this invention.
Figure 3A:
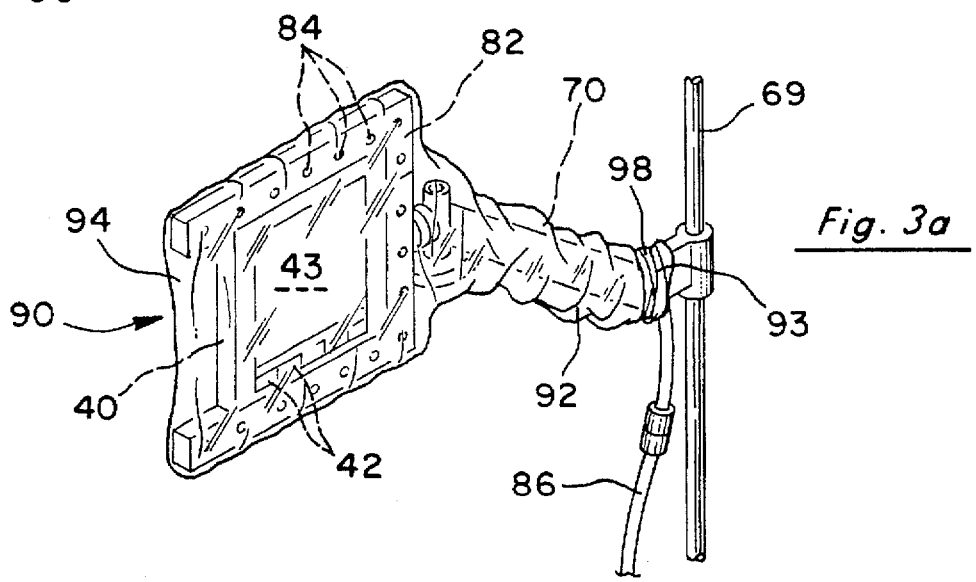
FIG. 3a is a fragmentary perspective view of the second embodiment of this invention illustrating the sterile drape covering the video monitor module.

According to a second embodiment of the sterile encapsulated operating room flat panel video monitor and flat panel video support device 10a, as shown in FIG. 3, a video support stand 60 is provided with a monitor mount 80 secured to a monitor module 40 in a desired location within an operating room. The structure of the video support stand 60 may include vertical members 62 for securing shelves 68. The bottom ends of vertical member 62 attach to base member 64. As with the first embodiment, a plurality of casters 66 or other wheel-like mechanisms may be mounted to base member 64 enabling the video support stand 60 to be transported from one location to another.

Vertical support 69 is connected to the support stand 60 at its upper end and lower ends to a shelf 68 and base member 64, respectively. Support arm 70 includes sleeve 71 which slips over vertical support 69. Joint 72 interconnects the free end of support arm 70 to monitor mount 80 enabling monitor mount 80 to be rotated to a desired position. As shown in FIG. 3, support arm 70 may be selectively placed along the length of the vertical support 69 in a desired position. Monitor mount 80 includes monitor mounting frame 82 which differs from the monitor mounting frame 32 of the first embodiment in that monitor mounting frame 82 is adapted to receive the monitor module 40 by simply sliding the monitor module 40 into the space between opposing sides of parallel mounting frame extensions 83. The monitor module 40 may be held in place by a series of grooves (not shown) formed on mounting frame extensions 83 and corresponding to grooves on the monitor module 40. Alternatively, monitor module 40 may be mounted to monitor mount 80 as by screws, bolts or as otherwise well known by those skilled in the art. A plurality of vacuum apertures 84 are formed on mounting frame 82 and communicate with vacuum line 86 via internal vacuum passages (not shown) formed in mounting frame 82. Vacuum line 86, in turn, communicates with an external vacuum line 88 by means of coupling 87.

Sterile drape 90 is positionable over monitor mount 80 and extends over adjacent support arm 70. When placed in position for use, the closed distal end 94 of drape 90 fits snugly against frame extensions 83 and the folded portion 96 of the drape 90 may be unrolled at the open proximal end 93 thereof to extend over an appropriate length of the support arm 70. Although being illustrated as a single piece, support arm 70 may comprise a plurality of pieces connected by hinges to allow the arm 70 to be folded or unfolded to a desired length. Tape 98 or an appropriate adhesive seal may be used to secure the open proximal end 93 of the drape 90 and to provide an airtight barrier when a vacuum is drawn on the drape 90. A tightly fit drape 90 ensures that no distortion of the monitor module screen 43 occurs because of the drape.

Figure 3B:
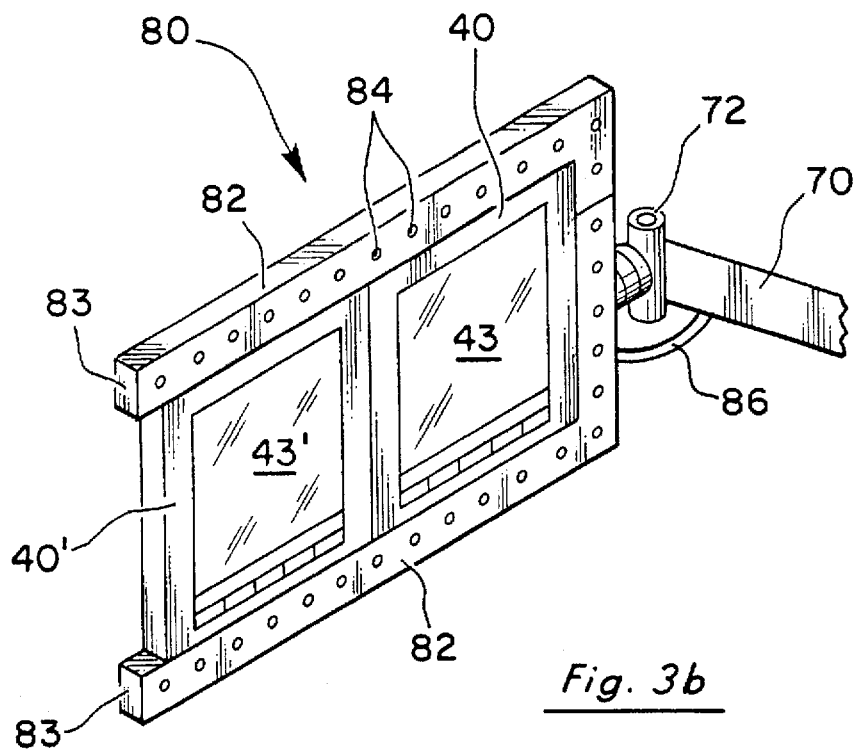
FIG. 3b is a fragmentary perspective view of a modified second embodiment wherein two monitor modules are provided in a side-by-side arrangement.
Figure 3C:
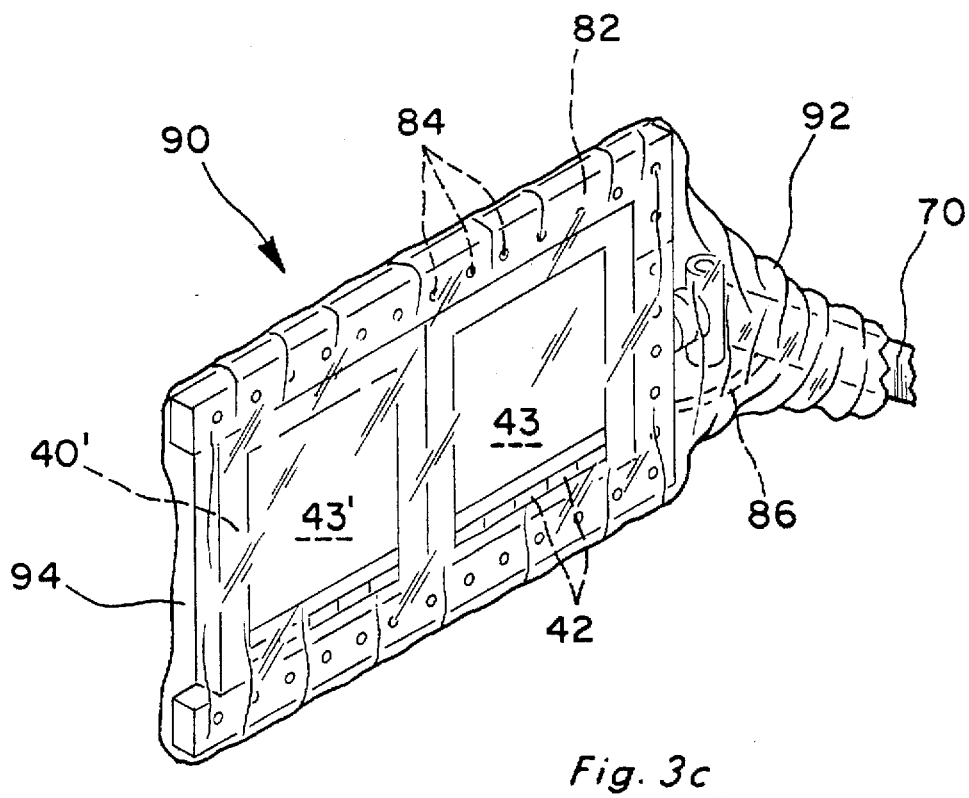
FIG. 3c is a fragmentary perspective view of the modified second embodiment illustrating the sterile drape covering the pair of side-by-side monitor modules.

In a modified second embodiment of this invention as shown in FIGS. 3b and 3c, the video support stand 60 may be provided with a monitor mount 80 which is large enough to accommodate two side-by-side monitor modules, 40 and 40'. As illustrated in FIG. 3b, the monitor mounting frame 82 may be extended to receive the second monitor 40'. Accordingly, a surgeon can simultaneously view two different surgical areas in a side-by-side manner by viewing screen 43 and 43'. Particularly in complex surgical procedures wherein more than one surgical area must be monitored, the capability to have a side-by-side view of remote surgical areas is advantageous.

As shown in FIG. 3c, module 40 and module 40' may both be covered by the same sterile drape 90. Accordingly, a separate drape structure is unnecessary to provide a sterile barrier for both of the monitors housed within monitor mount 80. Although two side-by-side monitors have been illustrated in FIGS. 3b and 3c, it will be understood by those skilled in the art that mounting frame 82 may be further lengthened to accommodate any number of monitor modules which may be placed in the side-by-side manner or even in vertically stacked positions.

In a third embodiment of the sterile operating room video and video monitor support device of this invention, as shown in FIG. 4, the device 10b may include a support arm 100 which connects directly to the side rail R of an operating room table T. A C-clamp 106 or other appropriate type of bracket holds support arm 100 against rail R wherein adjuster 108 allows the support arm 100 to be displaced along the length of side rail R. The free end of support arm 100 includes at least one hanger(s) or hook(s) 102 which engage corresponding eye bolts 104 formed on monitor mount 116. The monitor mount 116 shown in the embodiment of FIG. 4 is similar to the monitor mount 30 illustrated in FIG. 2a. That is, monitor mount 116 includes a plurality of apertures 118 which communicate with a vacuum line 86 which, in ram, connects to an operating room vacuum source (not shown). The same type of drape 90 which is shown in the embodiment in FIG. 3 may also be utilized in the embodiment shown in FIG. 4. That is, the drape is placed over the monitor mount 116 which contains the monitor module 40 and is then extended over an appropriate length of support arm 100. Tape or adhesive 98 is used to secure the open proximal end 93 of the drape to ensure that a proper vacuum may be drawn on the drape 90.

Also, according to the third embodiment of this invention, support arm 70 may be an existing arm support supplied with most operating room tables known in the art as "ether screen supports." If such an existing arm is used, it may be enclosed inside a standard surgical drape (not shown). Then, monitor module 40 may be enclosed within drape 90. Tape or adhesive 98 is also used to ensure that a proper vacuum may be drawn on the drape 90. Monitor module 40 which is enclosed within drape 90 may then be attached to arm 70 which is itself enclosed within the separate standard surgical drape. One advantage of providing a drape for arm 70 and a drape for monitor module 40 is that monitor module 40 may be replaced with another monitor without having to expose arm 70 to the sterile field of the surgical area. Whether the drape 90 extends over the monitor module 40 and support arm 70, or whether the support arm 70 has its own separate drape, the drape or drapes should extend at least four to six feet or more to ensure that the arm 70 and any cables extending from monitor module 40 are isolated from the sterile field of the surgical area.

Although monitor module 40, monitor module 40', monitor mount 80 and support arm 100 are illustrated as being covered by a drape, it will be understood that this structure which may reside in the sterile field can be sterilized by an autoclave or the like, thus eliminating the need for a drape.

In a fourth embodiment of the sterile operating room video monitor and video monitor support device 10c of this invention, as shown in FIG. 5, a support assembly 120 is provided which includes a base 122 which connects to a vertical support 124. Vertical support 124 may be uniform in thickness or diameter, or may further include a telescopic portion 126 which enables a standard video monitor V mounted on support platform 128 to be positioned at a desired location. In lieu of the standard video monitor V, a laptop computer (not shown) can be mounted on support platform 128. A plurality of casters or wheels 123 may be mounted to base 122 to enable the support assembly 120 to be transported to the desired location. Large sterile drape 110 is positioned over the video monitor V and downwardly extends over the vertical support 124. If a laptop computer is used, a drape such as drape 50 may be used so that monitor portion 56 covers the screen of the laptop computer. A vacuum port 112 is formed on the drape 50/110 and receives vacuum line 114 which, in turn, communicates with an appropriate operating room vacuum source. Tape or adhesive 130 is applied to the open proximal end of the drape 50/110 to ensure a vacuum can be drawn thereon.

The operation of the sterile operating room video monitor and video monitor support can best be seen in FIG. 1. As shown, the video support stand 12 is positioned adjacent to the operating room table T and the telescopic portion 20 of the support arm 18 extends over the patient's P body. In the type of surgical procedure being conducted, the surgeon S is standing toward the foot of the operating table T and observes the monitor module 40 in a visually aligned position with respect to the endoscope E which is inserted into the incision I. Because of the proximity of the monitor module 40 with the respect to both the surgeon S and the surgical site, the surgeon S may manipulate the image produced on the module screen 43 without having to turn away from the surgical site or by having another operating room person adjust the image for the surgeon. The sterile field is properly protected from contamination by use of the sterile drape which is placed over the monitor mount and extends downwardly over support arm 18. In a normal operating procedure, the endoscope E has a drape D attached at its proximal end which covers the trailing cables of the endoscope/video camera combination.

Although the application of the foregoing invention is particularly suited for surgery as conducted by medical doctors, the above-described invention is equally applicable and useful in dental surgery or dental procedures. Thus, each of the above-identified embodiments can be used by a dentist or oral surgeon who may wish to view the mouth area of a patient. Therefore, it will be understood that the invention disclosed herein is not restricted solely to surgical procedures conducted by medical doctors, but also extends to any type of procedure wherein viewing of a patient is desired.

In accordance with the invention described above, numerous problems associated with the use of video equipment in endoscopic procedures can be overcome. Since the video support stand 12 provides a means by which a surgeon may position a video image of the surgical site, the surgeon is able to maintain visual alignment with respect to the surgical area which greatly enhances the surgeon's ability to manipulate an endoscope. Because of the self-contained monitor module which is small and lightweight, and also has integral switches for controlling the type of image viewed, the surgeon may easily adjust the type of image to be viewed as well as position the monitor module with a minimum amount of disruption during a surgical procedure. By the use of the sterile drape which completely encloses a desired portion of the video support stand and monitor module which may be in contact with the sterile field of the operating room, sterility is not sacrificed at the cost of improved imaging capability.

This invention has been described in detail with reference to particular embodiments thereof, but it will be understood that various other modifications can be effected within the spirit and scope of this invention.

What is claimed is:

1. In combination, a video support stand and sterile drape for supporting a video monitor and enclosing the video monitor therein, said combination comprising:

a first video monitor;

a video support stand including a monitor mounting frame for releasably holding the first video monitor in a desired position, said frame further including interior edges defining an opening through which the first video monitor may be viewed; and a sterile drape including a flexible body portion, an inner surface defining an interior open space for enclosing the first video monitor therein, and a substantially transparent window portion integral with said flexible body portion and positionable over the first video monitor enabling an image produced on the first video monitor to be viewed without distortion, said window portion further including outer edges for releasable engagement with said interior edges of said monitor mounting frame.

2. The combination, as claimed in claim 1, wherein:

said substantially transparent window portion is substantially rigid.

3. The combination, as claimed in claim 1, wherein said window portion further includes:

a raised portion integral with said outer edges.

4. The combination, as claimed in claim 1, further including:

a second video monitor placed adjacent said first video monitor within said monitor mounting frame and positionable within said sterile drape enabling separate images to be viewed on said first video monitor and said second video monitor.

5. In combination, a video support stand and sterile drape for supporting a video monitor and enclosing the video monitor therein, said combination comprising:

a video monitor;

a video support stand including a monitor mounting frame for releasably holding the video monitor in a desired position, said frame further including interior edges defining an opening through which the video monitor may be viewed; and a sterile drape including a flexible body portion, an inner surface defining an interior open space for enclosing the video monitor therein, and a substantially transparent window portion integral with said flexible body portion and positionable over the video monitor enabling an image produced on the video monitor to be viewed without distortion, said window portion further including means for releasably engaging said monitor mounting frame.

6. The combination, as claimed claim 5, wherein:

said substantially transparent window portion is substantially rigid.

7. The combination, as claimed in claim 5, wherein said engaging means includes:

a raised portion formed on said engaging means.

* * * * *

UNITED STATES PATENT AND TRADEMARK OFFICE
CERTIFICATE OF CORRECTION

PATENT NO.   :   5,732,712
DATED        :   March 31, 1998
INVENTOR(S)  :   Edwin L. Adair It is certified that error appears in the above-identified patent and that said Letters Patent is hereby corrected as shown below:

Column 5, line 19, delete "10"; and
    Column 8, line 1, delete "ram" and insert --turn--.

Signed and Sealed this

Twenty-first Day of July, 1998

Attest:

BRUCE LEHMAN

*Attesting Officer*             *Commissioner of Patents and Trademarks*

UNITED STATES PATENT AND TRADEMARK OFFICE
CERTIFICATE OF CORRRECTION

PATENT NO. : 5,732,712
DATED : March 31, 1998
INVENTOR(S) : Edwin L. Adair It is certified that error appears in the above-identified patent and that said Letters Patent is hereby corrected as shown below:

On the title page: Item [56]

U. S. PATENT DOCUMENTS

| EXAMINER INITIAL | | PATENT NUMBER | | | | | | ISSUE DATE | PATENTEE | CLASS | SUBCLASS | FILING DATE IF APPROPRIATE |
|---|---|---|---|---|---|---|---|---|---|---|---|---|
| | | 4 | 6 | 2 | 5 | 7 | 3 | 1 | 12/02/86 | Quedens, et al. | | | 10/10/84 |
| | | 5 | 1 | 2 | 2 | 9 | 0 | 4 | 06/16/92 | Fujiwara, et al. | | | 10/22/90 |
| | | 5 | 3 | 5 | 1 | 6 | 7 | 6 | 10/04/94 | Putman | | | 02/08/93 |

Signed and Sealed this

Twelfth Day of October, 1999

Attest:

Q. TODD DICKINSON

*Attesting Officer*    *Acting Commissioner of Patents and Trademarks*